United States Patent [19]

Damani

[11] Patent Number: 5,114,718
[45] Date of Patent: May 19, 1992

[54] SUSTAINED RELEASE COMPOSITIONS FOR TREATING PERIODONTOL DISEASE

[75] Inventor: Nalinkant C. Damani, Cincinnati, Ohio

[73] Assignee: The Procter & Gamble Company, Cincinnati, Ohio

[21] Appl. No.: 585,445

[22] Filed: Sep. 20, 1990

[51] Int. Cl.$^5$ .............................................. A61F 13/00
[52] U.S. Cl. .................... 424/422; 424/434; 424/435
[58] Field of Search ................. 424/422, 434, 435

[56] References Cited

U.S. PATENT DOCUMENTS

| | | | |
|---|---|---|---|
| Re. 33,093 | 10/1989 | Schiraldi et al. | 424/676 |
| 307,537 | 11/1884 | Foulks | 424/435 |
| 4,175,326 | 11/1979 | Goodson | 433/80 |
| 4,250,163 | 2/1981 | Nagai et al. | 424/14 |
| 4,569,837 | 2/1986 | Suzuki | 424/435 |
| 4,764,377 | 8/1988 | Goodson | 424/435 |
| 4,788,062 | 11/1988 | Gale et al. | 424/449 |
| 4,789,662 | 12/1988 | Thomas-Leurquin | 424/422 |

FOREIGN PATENT DOCUMENTS 2085299  4/1982  United Kingdom ............... 424/435

*Primary Examiner*—Thurman K. Page
*Assistant Examiner*—D. Gabrielle Phelan
*Attorney, Agent, or Firm*—Douglas C. Mohl; Jack D. Schaeffer; Richard C. Witte

[57] ABSTRACT

This invention relates to devices/compositions and methods for treating diseases of the oral cavity in humans and lower animals using non-biodegradable devices/compositions which are biocompatible but not bioerodible for releasing drugs in or around a periodontol pocket or gingival sulcus.

10 Claims, No Drawings

SUSTAINED RELEASE COMPOSITIONS FOR TREATING PERIODONTOL DISEASE

TECHNICAL FIELD

This invention relates to compositions/devices for treating diseases of the oral cavity which compositions/devices are placed in or around the periodontol pocket or gingival sulcus. The invention also relates to methods of using the compositions/devices in humans and lower animals suffering from such diseases.

Periodontal disease, for example, is a major cause of tooth loss in adults. Tooth loss from periodontol disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontol disease, it does not necessarily prevent or eliminate its occurrence. This is because microorganisms contribute to both the initiation and progress of periodontol disease. Thus, in order to prevent or treat periodontol disease, these microorganisms must be suppressed by some means other than simple mechanical scrubbing. Towards this end, there has been a great deal of research aimed at developing therapeutic dentifrices, mouthwashes, and methods of treating periodontol disease which are effective in suppressing these microorganisms.

Recent developments in the art are directed toward delivering the therapeutic agent directly to the periodontol pocket, in some cases in a controlled release formulation. Goodson et al. have described the use of a drug-filled polymer hollow fiber. (J. M. Goodson et al., "Periodontal Therapy by Local Delivery of Tetracycline", *J. Clin. Periodontol.* 6, 83 (1979), J. Lindhe et al., "Local Tetracycline Delivery Using Hollow Fiber Devices in Periodontal Therapy", *J. Clin. Periodontol.* 6, 141 (1979) and R. L. Du et al., "Monolithic Fibers for Controlled Delivery of Tetracycline", in *Proc. Ninth Int. Symposium on Controlled Release of Bioactive Materials*, Ft. Lauderdale, Fla., July (1982). This device is tied around a tooth and gently pressed below the margin of the gingiva so that it resides in the periodontol pocket, and is capable of delivering an effective dose of 2.5 micrograms of tetracycline per day per periodontol pocket for a prolonged period of a week or more. Similar results have been obtained by Coventry and Newman (J. Coventry and H. N. Newman, "Experimental Use of a Slow Release Device Employing Chlorhexidine Gluconate in Areas of Acute Periodontal Inflammation", *J. Clin. Periodontol.* 9, 129 (1982) and Addy et al. (M. Addy et al., "The Development and in vitro Evaluation of Acrylic Strips and Dialysis Tubing for Local Drug Delivery", *J. Periodontol.* 53, 693 (1982) using acrylic strips 1 mm or more long, impregnated with chlorhexidine, tetracycline or metronidazole, which were inserted into the periodontol pocket with tweezers. Such a strip, formed from ethylcellulose impregnated with metronidazole, is disclosed by Loesche in U.S. Pat. No. 4,568,538 (February 1986). Another strip, employing a water soluble polymer of a particular elasticity and viscosity, is disclosed by Suzuki et al. in U.S. Pat. No. 4,569.837.

In addition to the above approaches, the prior art also discloses using putty-like compositions containing an antimicrobial for insertion into the periodontol pocket. A material disclosed as suitable is a copolymer of lactide and glycolide. See U.S. Pat. No. 4,650,665, Mar. 17, 1987 to Kronenthal et al., incorporated herein by reference.

The present inventor has found that a small chip, cone or strip loaded to a fairly high level with drug active can provide excellent release of the active into or around the periodontol pocket.

It is, therefore, an object of the present invention to provide devices/compositions suitable for use in or around the periodontol pocket.

It is a further object of the present invention to provide devices/compositions which are constructed of particular polymers.

It is still a further object of the present invention to provide a method of treating periodontol disease.

All percentages and ratios used in here are by weight unless otherwise indicated.

All measurements are made at 25° C. unless otherwise indicated.

SUMMARY OF INVENTION

The present invention relates to devices/compositions and methods for treating diseases of the oral cavity by inserting the devices/compositions into the periodontol pocket or around said pocket of humans and/or lower animals suffering from such diseases. The devices/compositions comprise biocompatible, non-bioerodible polymers and an agent providing relief of oral cavity diseases. The devices/compositions are flexible and solid and have approximate size and shape for simple placement at a disease site.

DETAILED DESCRIPTION OF THE INVENTION

The essential as well as optional components of the devices/compositions of this invention are described below.

Biocompatible/Non-Bioerodible Polymers

The polymers which are useful in forming the compositions/articles of the present invention include any polymer which is not bioerodible, is biocompatible and is capable of being formed into a solid. Included are polymers such as polyurethanes, ethylene vinyl acetate copolymers, collagen, poly isobutylene, cellulosic polymers, ethylene vinyl alcohol copolymers, polystyrene, polyvinyl chloride, polycarbonate, and polyethylene among many others.

The preferred polymers are ethylene vinyl acetate, poly isobutylene and polyurethane with ethylene vinyl acetate being the preferred material.

Drug Active

The drugs useful for use in the present devices/compositions are varied and many and include any agent which provides treatment or prevention management of diseases of the oral cavity. Some therapeutic agents which are amenable to delivery by this means and are potentially of value for periodontol therapy, include (but are not limited to) and antibacterial and antifungal agents such as iodine, triclosan sulfonamides, mercurials, bisbiguanides or phenolics; antibiotics such as the tetracyclines, neomycin, kanamycin, metronidazole, or clindamycin; antiinflammatory agents such as aspirin, naproxen, ibuprofen, flurbiprofen, indomethacin, eugenol, or hydrocortisone; anticalculus agents such as any of the soluble pyrophosphate salts some of which are described in U.S. Pat. No. 4,515,772, May 7, 1985 to Parran incorporated herein by reference; immune-suppressive or stimulatory agents such as methotrexate or levamasole; dentinal desensitizing agents such as strontium chloride or sodium fluoride; odor masking agents such as peppermint oil or chlorophyll; immune reagents such as immunoglobulins or antigens; local anesthetic agents such as lidocaine or benzocaine; nutritional agents such as amino acids, essential fats, and vitamin C; antioxidants such as alpha-tocopherol and butylated hydroxy toluene; lipopolysaccharide complexing agents such as polymyxin; or peroxides such as urea peroxide. It is recognized that in certain forms of therapy, combinations of these agents in the same delivery system may be useful in order to obtain an optimal effect. Thus, for example, an antibacterial and an antiinflammatory agent may be combined in a single delivery system to provide combined effectiveness.

The drug active is used at a level of from about 0.5% to about 95%, preferably from about 15% to about 85%, most preferably from about 20% to about 80% of the devices/compositions. The devices/compositions, for example, are designed to release drug to provide steady state average concentrations of active of from about 10 µg to about 5000 µg, preferably from about 25 µg to about 2500 µg, most preferably from about 50 µg to about 2000 µg per milliliter of the gingival crevicular fluid of a treated periodontol pocket, per one device unit. The steady state release rates can be altered by varying component ratios of the compositions, as well as by amount of device at a treatment site. The steady state conditions are preferably used since initial bursts are accounted for as well as delays in release. For example, in the case of a ten (10) day therapy, average steady state is generally reached in about one to two days.

Optional Components

In addition to the drug active, the devices/compositions of the present invention may include a variety of optional components. Such components include, but are not limited to, surfactants, viscosity controlling agents, complexing agents, antioxidants, other polymers such as carboxymethyl cellulose, gums such as guar gum, waxes/oils such as castor wax, castor oil, glycerol, dibutyl phthalate and di(2-ethylhexyl) phthalate as well as many others. If used, these optional components comprise from about 0.1% to about 20%, preferably from about 0.5% to about 5% of the total composition/device.

The devices/compositions of this invention are in shapes such as strips, chips or cones. The sizes of these shapes will generally fall into the following ranges:

Strips

| Average Thickness: | 0.75 (±0.5 mm) |
| --- | --- |
| Average Width: | 1.0 (±0.5 mm) |
| Average Length: | Cut as needed to fit a pocket, generally ranging from about 3 mm to about 12 mm |

Chips

| Average thickness: | 0.75 (±0.5 mm) |
| --- | --- |
| Average width of pointed end: | 0.3 (±0.25 mm) |
| Average width of wider end: | 1.5 (±0.5 mm) |
| Average length: | 15 (±5 mm) |

The length is cut at either end to fit a periodontol cavity by a dental professional at the time of use.

Cones

| Average pointed end diameter: | 0.25 (±0.2 mm) |
| --- | --- |
| Average thicker end diameter: | 1.5 (±0.5 mm) |
| Average length of cone: | 15 (±5 mm) |

The length is cut at either end to fit a periodontol cavity by a dental professional at the time of use.

METHOD OF MANUFACTURE

Method of manufacturing the devices/compositions of this invention are disclosed following the Examples for the purpose of illustration.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLE I

The following is an exemplary composition/device of the present invention.

|  | Parts per 100 |
| --- | --- |
| Tetracycline hydrochloride | 70 |
| Ethylene-vinyl Acetate | 30 |

EXAMPLE 2

The following is another exemplary composition/device of the present invention.

|  | Parts per 100 |
| --- | --- |
| Metronidazole | 57 |
| Bis(2-ethylhexyl) Phthalate | 3 |
| Ethylene-vinyl Acetate | 40 |

Bis(2-ethylhexyl) phthalate is dioctyl phthalate, and is used as a plasticizer to increase diffusion of a drug from the polymer.

EXAMPLE 3

The following is another exemplary composition/device of the present invention.

|  | Parts per 100 |
| --- | --- |
| Minocycline hydrochloride | 60 |
| Sodium chloride | 5 |
| Ethylene-vinyl Acetate | 35 |

Sodium chloride, as a soluble salt, provides an increase in internal osmotic pressure to increase drug release from the device.

EXAMPLE 4

The following is yet another exemplary composition of the present invention.

|  | Parts per 100 |
| --- | --- |
| Clindamycin hydrochloride | 30 |
| Liquid paraffin | 7 |
| Poly isobutylene (low molecular weight) | 26 |
| Poly isobutylene (high molecular weight) | 37 |

Liquid paraffin or mineral oil is a solvent isobutylene.

EXAMPLE 5

The following is another exemplary composition of the present invention.

|  | Parts per 100 |
| --- | --- |
| Chlorhexidene diacetate | 35 |
| Tetra sodium pyrophosphate | 10 |
| Polyurethane | 55 |

Pyrophosphate is included to provide effects on dental calculus.

EXAMPLE 6

The following is another exemplary composition of the present invention.

|  | Parts per 100 |
| --- | --- |
| Ciprofloxacin | 30 |
| Poly isobutylene | 20 |
| Polypropenoic acid | 10 |
| Polyurethane | 40 |

Polypropenoic acid is included in this example to absorb subgingival fluid, to keep the application site dry for the poly isobutylene component to develop adhesiveness at the application site.

The above described devices/compositions may be prepared by charging the polymer into a jacketed and heated mixer equipped with high shear Sigma type rotor blades. The mixer is heated to a temperature to melt or soften the polymer. The drug is added to the mixer and the mixing process is continued until a homogeneous blend is obtained. Additives other than a drug and polymer can be added to obtain a homogeneous blend.

The composition blend is removed from the mixer, and is compressed between platens of a hydraulic press such as a Carver press, using spacers to obtain the desired thickness. Although not necessary, it is desirable to have the platens of the hydraulic press jacketed, which allows heating and cooling of the material during the compression process. Upon compression, the material is obtained in form of a uniform thickness film. Devices of this development are cut into suitable size and shape using this film. Cone shaped devices, for example, are prepared from thin films having thickness of about 0.01 mm and rolling to form a cone shape.

Other alternative mixing and forming methods may be used to obtain devices/compositions of this invention. The appropriate sizes and shapes are set forth on page 5 of this application.

What is claimed:

1. A solid composition suitable for insertion into the periodontal pocket or the gingival sulcus of a person or lower animal suffering from diseases of the oral cavity comprising a non-biodegradable, biocompatible polymer selected from the group consisting of polyurethanes, ethylene vinyl acetate copolymers, collagen, poly isobutylene, ethylene vinyl alcohol copolymers, polyethylene polycarbonate, and polyvinyl chloride and a drug active selected from the group consisting of antiinflammatory agents, antimicrobials, antibiotics, peroxides, anesthetic agents, and vitamins in a concentration from about 0.5% to about 95% wherein said composition is in the form of a chip, cone or strip and wherein said composition provides steady state average concentrations of active of from about 10 $\mu$g to about 5000 $\mu$g, preferably from about 25 $\mu$g to about 2500 $\mu$g per milliliter of the gingival crevicular fluid of a treated periodontal pocket or gingival sulcus.

2. A composition according to claim 1 wherein the concentration of the drug active is from about 15% to about 85% and the active is selected from the tetracycline group of antibiotics.

3. A composition according to claim 1 wherein the composition is formed into a shape of a strip average having a width of about 1 mm, an average thickness of about 0.75 mm, and an average length of about 10 mm.

4. A composition according to claim 1 wherein the composition is formed into the shape of a cone having an average length of about 15 mm, an average diameter at the wide end of about 1.5 mm, and an average diameter at the pointed end of about 0.25 mm.

5. A composition according to claim 1 wherein the composition is formed into the shape of a chip having an average length of about 15 mm, an average width at the wide end of about 1.5 mm, and an average width of the pointed end of about 0.5 mm, and average thickness of about 0.8 mm.

6. A composition according to claim 5 wherein the polymer is ethylene vinyl acetate.

7. A composition according to claim 6 wherein the active is selected from the tetracycline group of antibiotics.

8. A method of treating diseases of the oral cavity in a person or lower animal suffering from such disease by placing into the periodontol pocket or around said pocket or gingival sulcus of said person or lower animal a composition according to claim 1.

9. A method according to claim 8 wherein the drug active is selected from the tetracycline group of antibiotics.

10. A method according to claim 9 wherein the composition is formed into the shape of a chip having an average length of about 10 mm, an average width of the wide end of about 1 mm, and an average width of the pointed end of about 0.2 mm, and average thickness of about 0.6 mm.

* * * * *